(12) United States Patent
Alferness et al.

(10) Patent No.: US 6,416,554 B1
(45) Date of Patent: Jul. 9, 2002

(54) LUNG REDUCTION APPARATUS AND METHOD

(75) Inventors: Clifton A. Alferness, Redmond, WA (US); Richard Y. Lin, Redwood City; Wilfred E. Jaeger, Portola Valley, both of CA (US)

(73) Assignee: Spiration, Inc., Redmond, WA (US)

( * ) Notice: Subject to any disclaimer, the term of this patent is extended or adjusted under 35 U.S.C. 154(b) by 0 days.

(21) Appl. No.: 09/379,973

(22) Filed: Aug. 24, 1999

(51) Int. Cl.[7] .................................................. A61F 2/36
(52) U.S. Cl. ....................................... 623/23.65; 600/37
(58) Field of Search ........................... 623/23.64, 23.65, 623/66.1, 11.11; 600/37; 128/898

(56) References Cited

U.S. PATENT DOCUMENTS 5,702,343 A  * 12/1997  Alferness ..................... 600/37
6,123,663 A     9/2000   Rebuffat
6,241,654 B1 *  6/2001   Alferness ..................... 600/37

* cited by examiner

Primary Examiner—Dinh X. Nguyen
Assistant Examiner—Urmi Chattopadhyay
(74) Attorney, Agent, or Firm—Graybeal Jackson Haley LLP

(57) ABSTRACT

An apparatus and method reduces the size of a lung. The apparatus includes a jacket of flexible fabric configured to cover at least a portion of the lung. A lace, carried by the jacket, collapses the jacket about the lung portion. The jacket may further include a drawstring circumscribing the jacket at the base for closing the open base of the jacket about the lung portion. The collapsing of the jacket may be employed for both reducing the size of the lung and maintaining the lung in a reduced size condition or the lung portion may be deflated prior to the placement of the jacket over the lung portion, in which case, the jacket serves to prevent re-expansion of the lung portion.

18 Claims, 4 Drawing Sheets

LUNG REDUCTION APPARATUS AND METHOD

BACKGROUND OF THE INVENTION

The present invention is generally directed to an apparatus and method for treating Chronic Obstructive Pulmonary Disease (COPD). The present invention is more particularly directed to such an apparatus and method which may be implanted in the human body to provide lung size reduction by constricting at least a portion of a lung.

Chronic Obstructive Pulmonary Disease (COPD) has become a major cause of morbidity and mortality in the United States over the last three decades. COPD is characterized by the presence of airflow obstruction due to chronic bronchitis or emphysema. The airflow obstruction in COPD is due largely to structural abnormalities in the smaller airways. Important causes are inflammation, fibrosis, goblet cell metaplasia, and smooth muscle hypertrophy in terminal bronchioles.

The incidence, prevalence, and health-related costs of COPD are on the rise. Mortality due to COPD is also on the rise. In 1991 COPD was the fourth leading cause of death in the United States and had increased 33% since 1979.

COPD affects the patient's whole life. It has three main symptoms: cough; breathlessness; and wheeze. At first, breathlessness may be noticed when running for a bus, digging in the garden, or walking up hill. Later, it may be noticed when simply walking in the kitchen. Overtime, it may occur with less and less effort until it is present all of the time.

COPD is a progressive disease and currently has no cure. Current treatments for COPD include the prevention of further respiratory damage, pharmacotherapy, and surgery. Each is discussed below.

The prevention of further respiratory damage entails the adoption of a healthy lifestyle. Smoking cessation is believed to be the single most important therapeutic intervention. However, regular exercise and weight control are also important. Patients whose symptoms restrict their daily activities or who otherwise have an impaired quality of life may require a pulmonary rehabilitation program including ventilatory muscle training and breathing retraining. Long-term oxygen therapy may also become necessary.

Pharmacotherapy may include bronchodilator therapy to open up the airways as much as possible or inhaled β-agonists. For those patients who respond poorly to the foregoing or who have persistent symptoms, Ipratropium bromide may be indicated. Further, courses of steroids, such as corticosterocds, may be required. Lastly, antibiotics may be required to prevent infections and influenza and pheumococcal vaccines may be routinely administered. Unfortunately, there is no evidence that early, regular use of pharmacotherapy will alter the progression of COPD.

About 40 years ago, it was first postulated that the tethering force that tends to keep the intrathoracic airways open was lost in emphysema and that by surgically removing the most affected parts of the lungs, the force could be partially restored. Although the surgery was deemed promising, the procedure was abandoned.

The lung volume reduction surgery (LVRS) was later revived. In the early 1990's, hundreds of patients underwent the procedure. However, the procedure has fallen out of favor due to the fact that Medicare stopped remitting for LVRS. Unfortunately, data is relatively scarce and many factors conspire to make what data exists difficult to interpret. The procedure is currently under review in a controlled clinical trial. However, what data does exist tends to indicate that patients benefited from the procedure in terms of an increase in forced expiratory volume, a decrease in total lung capacity, and a significant improvement in lung function, dyspnea, and quality of life.

Improvements in pulmonary function after LVRS have been attributed to at least four possible mechanisms. These include enhanced elastic recoil, correction of ventilation/perfusion mismatch, improved efficiency of respiratory musculature, and improved right ventricular filling.

Lastly, lung tranplantation is also an option. Today, COPD is the most common diagnosis for which lung transplantation is considered. Unfortunately, this consideration is given for only those with advanced COPD. Given the limited availability of donor organs, lung transplant is far from being available to all patients.

In view of the foregoing, there in a need in the art for a new and improved therapy for COPD. More specifically, there is a need for such a therapy which provides more permanent results than pharmacotherapy while being less traumatic than LVRS. The present invention is directed to an apparatus and method which provide such an improved therapy for COPD.

SUMMARY OF THE INVENTION

The present invention provides an implantable apparatus for reducing the size of a lung. The apparatus includes a jacket of flexible fabric configured to cover at least a portion of a lung and collapsing means carried by the jacket for collapsing the jacket about the lung portion.

The invention still further provides a method of reducing the size of a lung. The method includes the steps of disposing a jacket of flexible fabric over at least a portion of a lung. The collapsing of the jacket may serve to both reduce the size of the lung and maintain it in its reduced size condition. Alternatively, the lung portion may first be deflated whereupon the collapsed jacket serves to maintain the lung portion in a deflated, reduced size condition.

BRIEF DESCRIPTION OF THE DRAWINGS

The features of the present invention which are believed to be novel are set forth with particularity in the appended claims. The invention, together with further objects and advantages thereof, may best be understood by making reference to the following description taken in conjunction with the accompanying drawings, in the several figures of which like referenced numerals identify identical elements, and wherein:

DETAILED DESCRIPTION

Figure 1:
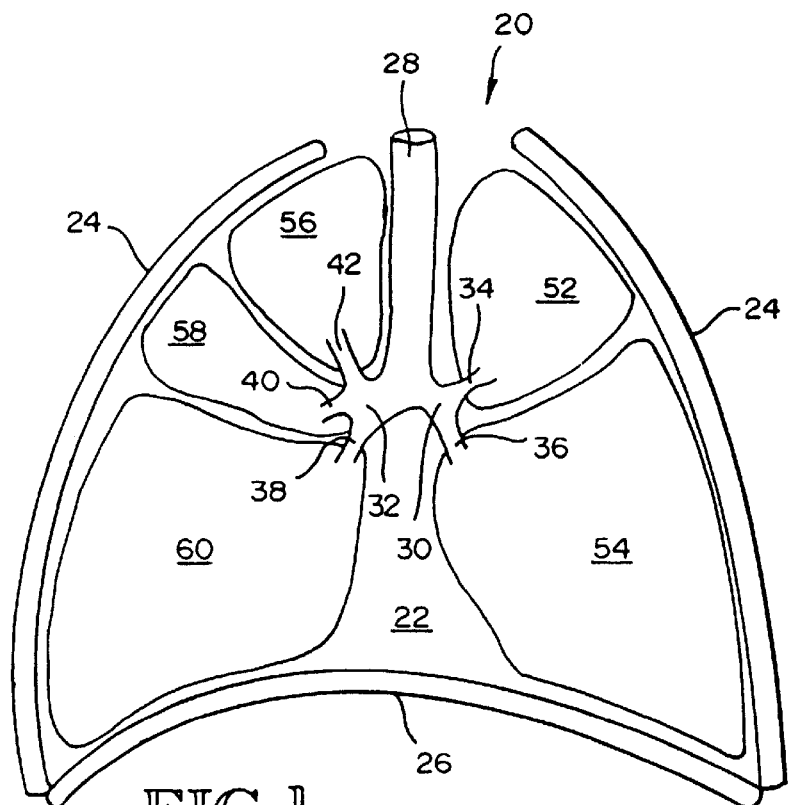
FIG. 1 is a simplified sectional view of a thorax illustrating a healthy respiratory system.

Referring now to FIG. 1, it is a sectional view of a healthy respiratory system. The respiratory system 20 resides within the thorax 22 which occupies a space defined by the chest wall 24 and the diaphragm 26.

The respiratory system 20 includes the trachea 28, the left mainstem bronchus 30, the right mainstem bronchus 32, and the bronchial branches 34, 36, 38, 40, and 42. The respiratory system 20 further includes left lung lobes 52 and 54 and right lung lobes 56, 58, and 60. Each bronchial branch communicates with a respective different portion of a lung lobe, either the entire lung lobe or a portion thereof.

Characteristic of a healthy respiratory system is the arched or inwardly arcuate diaphragm 26. As the individual inhales, the diaphragm 26 straightens to increase the volume of the thorax 22. This causes a negative pressure within the thorax. The negative pressure within the thorax in turn causes the lung lobes to fill with air. When the individual exhales, the diaphragm returns to its original arched condition to decrease the volume of the thorax. The decreased volume of the thorax causes a positive pressure within the thorax which in turn causes exhalation of the lung lobes.

Figure 2:
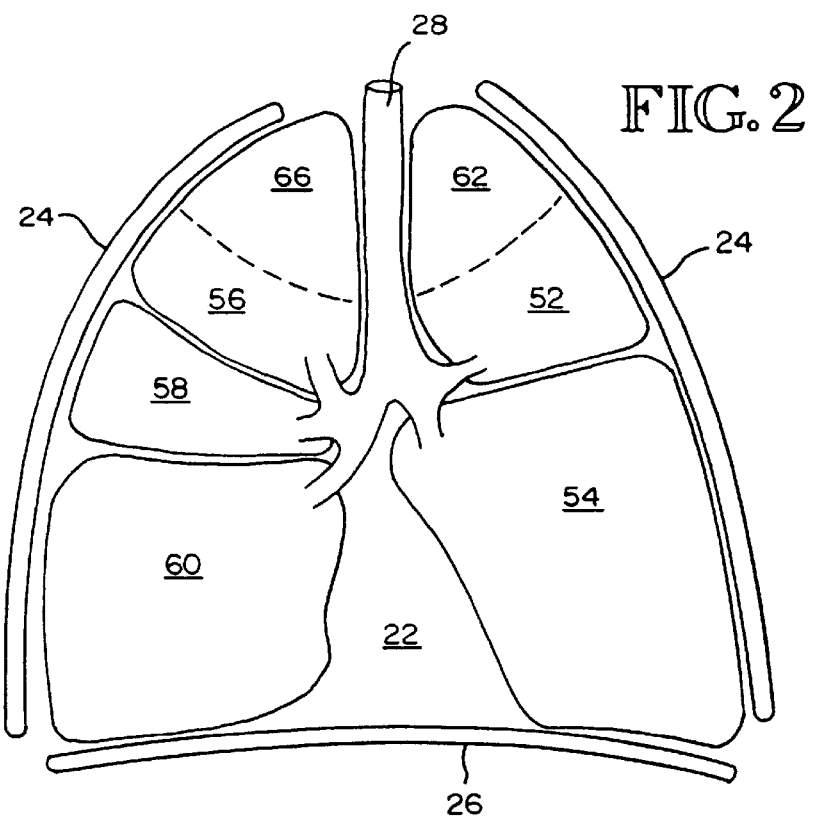
FIG. 2 is a sectional view similar to FIG. 1 but illustrating a respiratory system suffering from COPD.

In contrast to the healthy respiratory system of FIG. 1, FIG. 2 illustrates a respiratory system suffering from COPD. Here it may be seen that the lung lobes 52, 54, 56, 58, and 60 are enlarged and that the diaphragm 26 is not arched but substantially straight. Hence, this individual is incapable of breathing normally by moving the diaphragm 28. Instead, in order to create the negative pressure in the thorax 22 required for breathing, this individual must move the chest wall outwardly to increase the volume of the thorax. This results in inefficient breathing causing these individuals to breathe rapidly with shallow breaths.

It has been found that the apex portion 62 and 66 of the upper lung lobes 52 and 56, respectively, are most affected by COPD. Hence, the preferred embodiment will be described for treating the apex 66 of the right, upper lung lobe 56. However, as will be appreciated by those skilled in the art, the present invention may be applied to any lung portion without departing from the present invention.

The apparatus and method of the present invention treats COPD by deriving the benefits of lung volume reduction surgery without the need of performing lung volume reduction surgery. As will be seen hereinafter, the present invention contemplates permanent collapse of a lung portion or lung portions most affected. This leaves extra volume within the thorax for the diaphragm to assume its arched state for acting upon the remaining healthier lung tissue. As previously mentioned, this should result in improved pulmonary function due to enhanced elastic recoil, correction of ventilation/perfusion mismatch, improved efficiency of respiratory musculature, and improved right ventricle filling.

Figure 3:
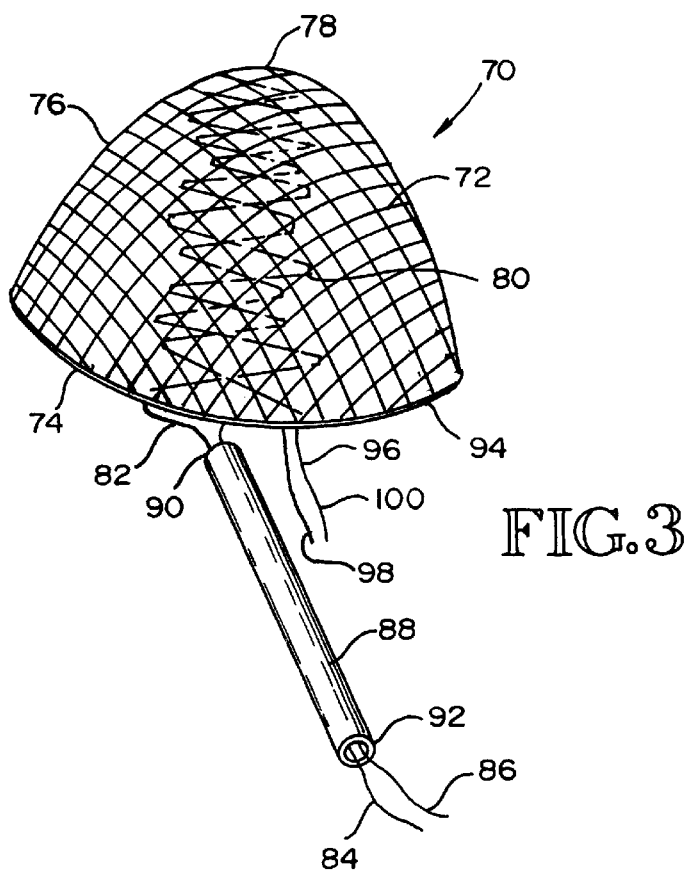
FIG. 3 is a perspective view illustrating a lung constriction apparatus embodying the present invention.

Referring now to FIG. 3, it illustrates a lung constriction apparatus 70 embodying the present invention. The apparatus 70 takes the form of a jacket 72 formed of a flexible fabric such as an open mesh of polyester. The jacket includes an open base 74 and a curved surface 76 extending from the open base 74 and terminating in a closed, domed-shape end or apex 78. The open base 74 is dimensioned to be applied over and to cover the lung portion to be reduced in size.

The constriction apparatus 70 further includes at least one lace 80 extending from the apex 78 to the base 74. The cord 82 forming the lace 80 has a pair of free ends 84 and 86 which are threaded through a guide tube 88 from the distal end 90 of the guide tube 88 to the proximal end 92 of the guide tube 88.

The guide tube 88 serves to maintain the free ends 84 and 86 of the cord 82 together. When the free ends 84 and 86 of the cord 82 are drawn while holding the guide tube distal end 90 adjacent the base 74, the jacket 72 is collapsed to reduce the inner volume of the jacket. This constriction of the jacket serves to collapse the jacket about the lung portion to be reduced in size.

As will be seen hereinafter, a plurality of laces may be carried by the jacket. As each lace is drawn, the jacket will be collapsed to a greater and controlled extent.

The jacket 72 further includes a piping 94 at the base 74. A draw string 96 is threaded through the piping to circumscribe the jacket 72 and the base 74. The draw string has a pair of free ends 98 and 100. As will be seen hereinafter, after the laces are drawn to collapse the jacket 72 about the lung portion, the free ends 98 and 100 of the draw string 96 may be pulled and drawn to close the open base 74 of the jacket 72 about the lung portion. This will provide additional constriction to assure that the lung portion does not reinflate. It also serves to cut off all blood circulation to the lung portion. This promotes infarction and fibrosis.

Figure 4:
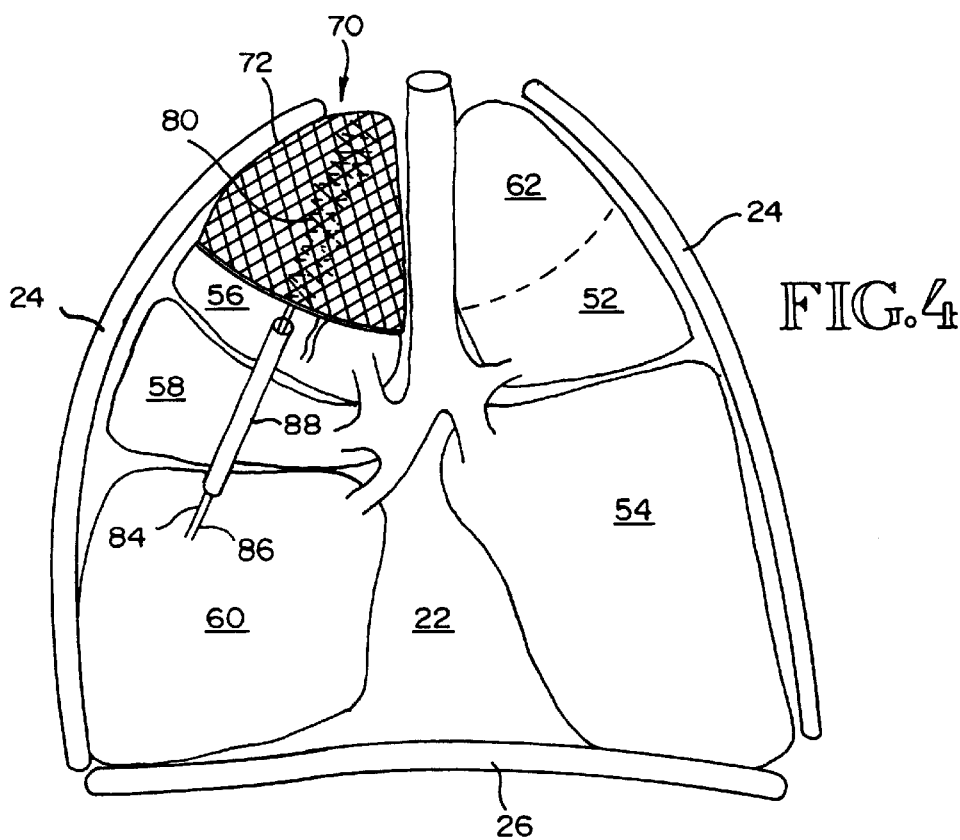
FIG. 4 is a sectional view of the respiratory system of FIG. 2 with a lung constriction apparatus embodying the present invention being disposed over a lung portion to be reduced in size.

Referring now to FIG. 4, it illustrates the constriction device 70 after it has been placed over the apex of the upper right lung lobe 56 to cover the lung portion 66 of the right upper lobe 56 referred to previously with respect to FIG. 2. The jacket 72 covers the lung portion 66. At this point, the free ends 84 and 86 of the cord forming the lace 80 have not been drawn.

Figure 5:
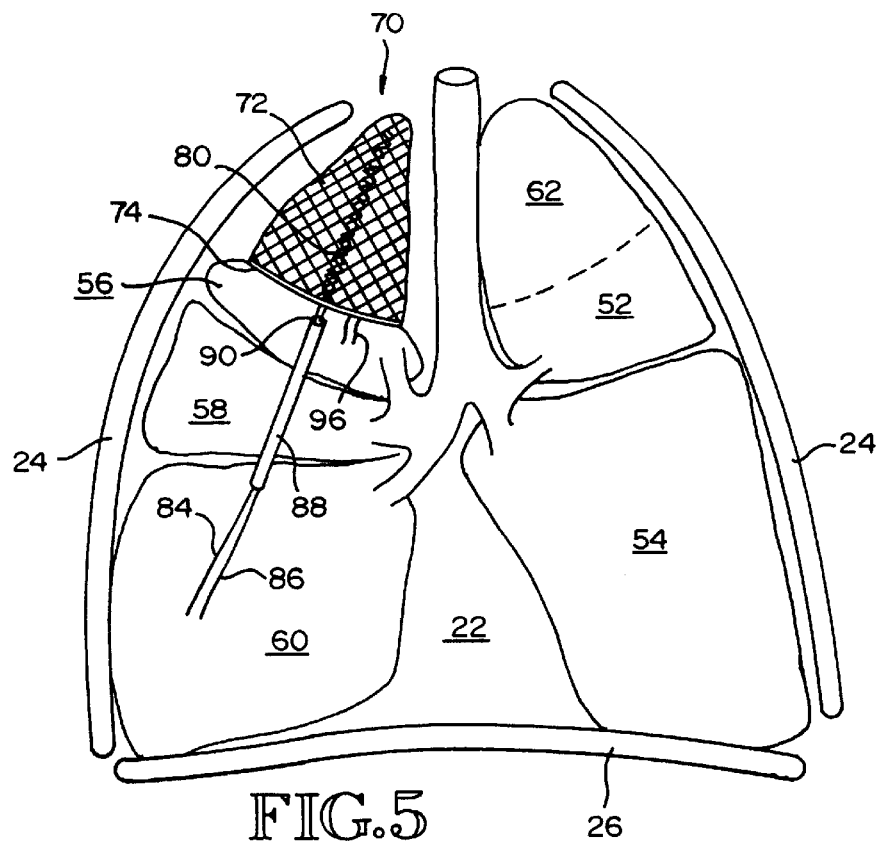
FIG. 5 illustrates an initial step in collapsing the lung constricting apparatus about the lung portion.

Referring now to FIG. 5, here it may be seen that the lace 80 has been drawn by the pulling of the free ends 84 and 86 of the lace cord while holding the guide tube 88 such that its distal end 90 is closely adjacent the base 74 of the jacket 72. As will be observed in FIG. 5, because the jacket 72 has been collapsed about the lung portion 66 of the upper lobe 56, the lung portion 66 has been reduced in size due to the constriction of the jacket 72.

Figure 6:
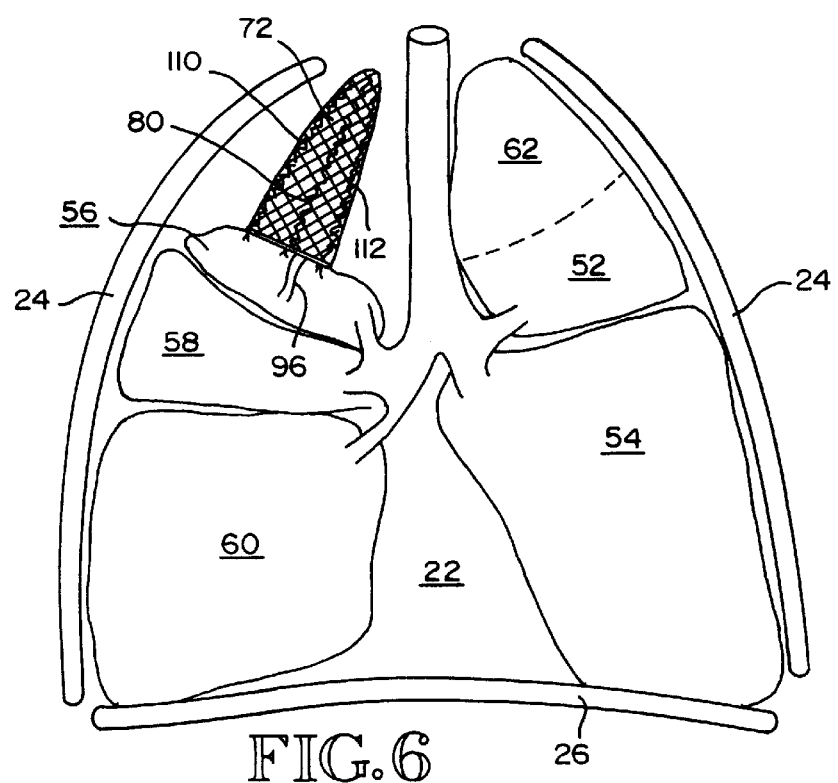
FIG. 6 illustrates a further step in collapsing the lung constriction apparatus.

FIG. 6 illustrates the jacket 72 with additional laces 110 and 112 which have also been drawn. When the laces are drawn tightly, the free ends of the cords forming the laces may be tied off and then cut as illustrated. The lung portion 66 of the upper right lobe 56 is now more fully reduced in size by the constriction of the jacket 72.

Figure 7:
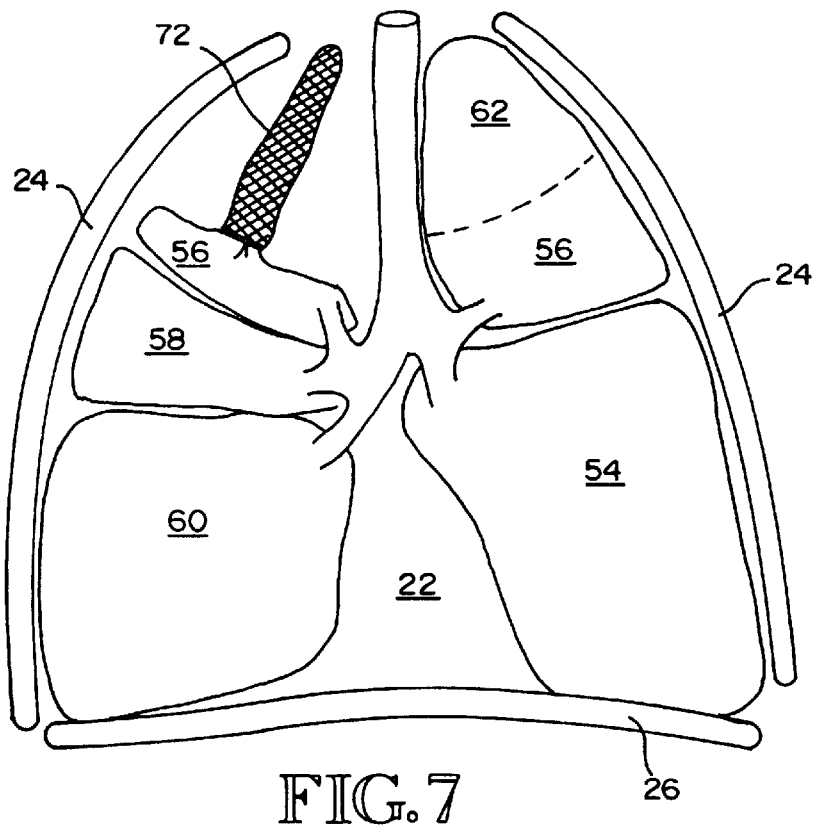
FIG. 7 illustrates the lung constricting apparatus being fully collapsed about the lung portion.

FIG. 7 illustrates the further constriction provided by the drawstring after being pulled. The free ends of the drawstring after being pulled may be then tied together and cut as illustrated. As can be seen in FIG. 7, the lung portion 66 of the upper right lobe 56 has been drastically reduced in size. Further, the drawstring constriction will cut off circulation to the lung portion 66 to promote infarction and fibrosis.

Figure 8:
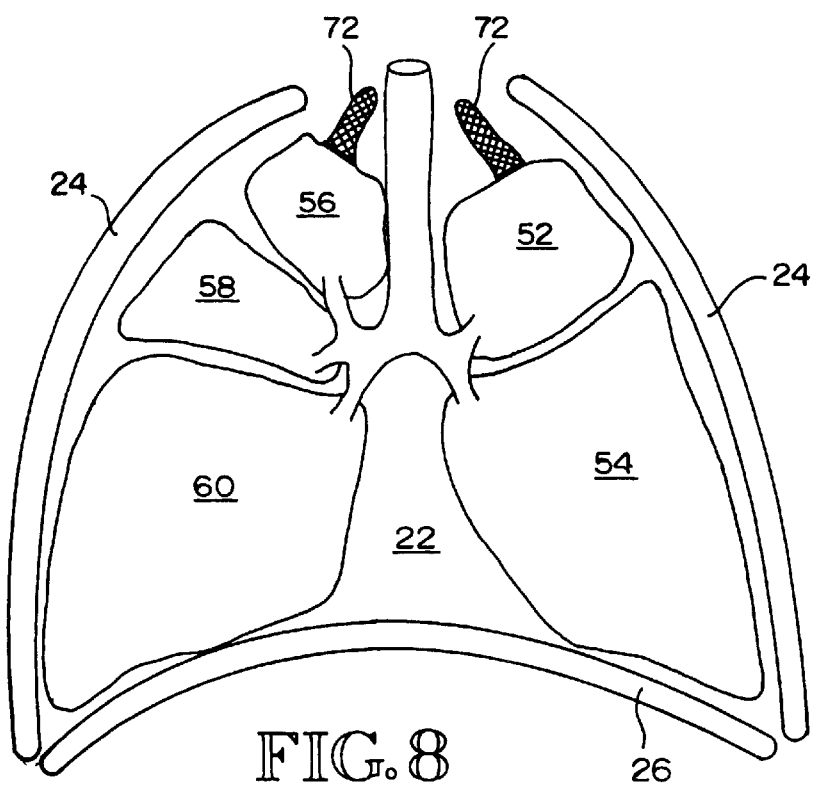
FIG. 8 illustrates the respiratory system after both left and right side lung portions have been reduced in size in accordance with the present invention.

FIG. 8 illustrates the respiratory system after both the lung portion 66 of the upper right lobe 56 and the lung portion 62 of the upper left lobe 52 have been treated as described above. Here it can be seen that the volumes of the right upper lung lobe 56 and left upper lung lobe 52 have been reduced in size by the jacket 72. This causes the lung lobes to occupy less volume within the thorax 22 to permit the diaphragm 26 to assume its arched state for acting upon the remaining healthier lung tissue. As previously mentioned, this should result in improved pulmonary function due to enhanced elastic recoil, correction of ventilation/perfusion mismatch, improved efficiency of respiratory musculature, and improved right ventricle filling.

As can thus be seen from the foregoing, the present invention provides an apparatus and method for treating COPD by lung volume reduction. The lung volume reduction is achieved through the permanent collapsing of one or more lung portions, or lobes, or portions of lobes. The foregoing is achieved without the need for removing lung tissue. Following the treatment, the lung tissue within the thorax will occupy a lesser volume than previously occupied providing room for the diaphragm to assume its arcuate state to assist in normal breathing and to achieve the benefits of lung volume reduction.

While particular embodiments of the present invention have been shown and described, modifications may be made. For example, while the jacket may be employed for reducing the size of a lung by constriction, the invention is not intended to be so limited. Rather, the lung portion may become deflated during surgery on its own or by other means known in the art. The jacket may then be placed on the lung portion while it is in a deflated condition. The jacket may then be collapsed about the lung portion to cinch down over the lung to maintain it in its deflated, reduced volume condition. The jacket would thus prevent re-expansion of the captured lung portion. The remaining portions of the lung may then be expanded, if necessary, by means known in the art. Hence, it is intended in the appended claims to cover all such changes and modifications which fall within the true spirit and scope of the invention.

What is claimed is:

1. An implantable apparatus for reducing the size of a lung comprising:
    a jacket of flexible fabric configured to be implanted and to cover only a portion of a lung; and
    collapsing means for collapsing the jacket about the lung portion to collapse the lung portion.

2. The apparatus of claim 1 wherein the flexible fabric is an open mesh material.

3. The apparatus of claim 1 wherein the jacket includes an opening for applying the jacket to the lung portion, and a closed end.

4. An implantable apparatus for reducing the size of a lung comprising:
    a jacket of flexible fabric configured to be implanted and to cover at least a portion of a lung; and
    collapsing means for collapsing the jacket about the lung portion, the jacket including an opening for applying the jacket to the lung portion, and a base defining the opening and being dimensioned to be applied over and to cover the lung portion to be reduced in size.

5. The apparatus of claim 4 wherein the collapsing means is carried by the jacket and comprises at least one lace extending from the closed end towards the base, the at least one lace including a cord having a pair of free ends which, when drawn, collapse the jacket about the lung portion.

6. The apparatus of claim 5 further including a guide tube having a distal end and a proximal end and wherein the free ends of the cord are threaded from the distal end of the guide tube to and through the proximal end of the guide tube.

7. The apparatus of claim 6 wherein the distal end of the guide tube is closely adjacent the base of the jacket.

8. The apparatus of claim 4 wherein the collapsing means includes a draw string circumscribing the jacket at the base, the draw string having a pair of free ends which, when drawn, close the open base of the jacket about the lung portion.

9. The apparatus of claim 1 wherein the flexible fabric is formed of polyester.

10. A method of reducing the size of a lung, the method including the steps of:
    disposing a jacket of flexible fabric over only a portion of a lung; and
    collapsing the jacket about the lung portion to collapse the lung portion.

11. The method of claim 10 wherein the flexible fabric is an open mesh material.

12. The method of claim 11 wherein the open mesh material is a polyester mesh.

13. The method of claim 10 including the step of providing the jacket with a closed end and an opening to permit disposing the jacket over the lung portion.

14. A method of reducing the size of a lung, the method including the steps of:
    disposing a jacket of flexible fabric over at least a portion of a lung;
    providing the jacket with a closed end and an opening to permit disposing the jacket over the lung portion; and
    collapsing the jacket about the lung portion to collapse the lung portion, wherein the collapsing step includes lacing a cord on the jacket from the closed end towards the opening, the cord when laced having a pair of free ends, and pulling on the free ends of the cord to cause the jacket to collapse about the lung portion.

15. The method of claim 14 wherein the collapsing step further includes tying the free ends of the cord together after the jacket is collapsed about the lung portion.

16. A method of reducing the size of a lung, the method including the steps of:
    disposing a jacket of flexible fabric over at least a portion of a lung;
    providing the jacket with a closed end and an opening to permit disposing the jacket over the lung portion; and
    collapsing the jacket about the lung portion to collapse the lung portion, wherein the collapsing step includes circumscribing the opening with a cord, the cord having a pair of free ends, and pulling on the free ends of the cord to collapse the opening of the jacket about the lung portion.

17. The method of claim 16 wherein the collapsing step further includes tying the free ends of the cord together after the opening of the jacket is collapsed about the lung portion.

18. The method of claim 10 including the further step of deflating the lung portion prior to disposing the jacket over the lung portion.

* * * * *